United States Patent
Bonk et al.

(10) Patent No.: US 11,781,158 B2
(45) Date of Patent: Oct. 10, 2023

(54) METHOD FOR CARRYING OUT THE COMBINED OPERATION OF A BIOETHANOL PRODUCTION UNIT AND A BIOGAS UNIT

(71) Applicant: VERBIO VEREINIGTE BIOENERGIE AG, Leipzig (DE)

(72) Inventors: Fabian Bonk, Leipzig (DE); Michael Schlimbach, Halle/Saale (DE); Oliver Lüdtke, Markkleeberg (DE)

(73) Assignee: VERBIO VEREINIGTE BIOENERGIE AG, Liepzig (DE)

( * ) Notice: Subject to any disclaimer, the term of this patent is extended or adjusted under 35 U.S.C. 154(b) by 59 days.

(21) Appl. No.: 17/308,456

(22) Filed: May 5, 2021

(65) Prior Publication Data
US 2022/0033860 A1 Feb. 3, 2022

(30) Foreign Application Priority Data
Aug. 3, 2020 (EP) ..................................... 20189166

(51) Int. Cl.
*C12P 7/10* (2006.01)
*C10L 5/44* (2006.01)

(52) U.S. Cl.
CPC ................. *C12P 7/10* (2013.01); *C10L 5/445* (2013.01); *C10L 2200/0476* (2013.01); *C12P 2201/00* (2013.01)

(58) Field of Classification Search
CPC .... C10L 2200/0476; C10L 5/445; C12F 3/10; C12P 2201/00; C12P 5/023; C12P 7/06; C12P 7/10
See application file for complete search history.

(56) References Cited

U.S. PATENT DOCUMENTS

2007/0141691 A1* 6/2007 Hirl ........................ C12M 21/12
435/161
2013/0142905 A1* 6/2013 Gibbons ................ A23J 1/125
426/656

FOREIGN PATENT DOCUMENTS

DE 10 2013 226991 A1 6/2015
DE 10 2014 001912 A1 9/2015
DE 2017/076380 A1 5/2017

OTHER PUBLICATIONS

European Extended Search Report dated Feb. 1, 2021, in connection with European Application No. 20189166.0.

* cited by examiner

*Primary Examiner* — Latosha Hines
(74) *Attorney, Agent, or Firm* — Norris McLaughlin, P.A.

(57) ABSTRACT

The present invention concerns a method for carrying out the combined operation of a bioethanol production unit and a biogas unit. The method comprises the following steps:
a) mashing corn meal from a dry milling step with at least 0.1 t of dry matter in the form of whole stillage and at least 0.1 m$^3$ of outflow from the biogas unit per tonne of corn meal,
b) feeding the mash from a) to a cooking stage with mash temperatures below the gelatinization temperature of the starch inn the corn meal, followed by an ethanol-forming fermentation step and then feeding the fermented mash to a distillation step,
c) feeding the whole stillage from b) to the mashing step in a) and to the biogas unit.

15 Claims, 2 Drawing Sheets

METHOD FOR CARRYING OUT THE COMBINED OPERATION OF A BIOETHANOL PRODUCTION UNIT AND A BIOGAS UNIT

This application claims foreign priority benefit under 35 U.S.C. § 119 of European Patent Application No. 20189166.0, filed Aug. 3, 2020, the disclosure of which is incorporated herein by reference.

The invention relates to a method for carrying out the combined operation of a bioethanol production unit and a biogas unit.

TECHNICAL BACKGROUND

The production of ethanol from corn is known and is a technology which is widely used on an industrial scale, particularly in the USA. Prior art units are those with the following process steps:

- Dry milling of corn with a screen size of 2-4 mm (Jacques, Lyons, & Kelsall, 2003), wherein a mass fraction of approximately 33% of the particles of the corn meal which is formed has a particle size of <0.59 mm (Jacques, Lyons, & Kelsall, 2003),
- Mashing corn meal with process liquids which are primarily composed of thin stillage (10-50% of the process liquids (Jacques, Lyons, & Kelsall, 2003)) and condensate from animal feed evaporation. The dry matter content (TS content) of the mash is approximately 29-33% (Jacques, Lyons, & Kelsall, 2003). The TS content of the thin stillage is approximately 4.4-7.8% (Jacques, Lyons, & Kelsall, 2003). In this regard, approximately 0.01-0.08 t TS is used in the form of thin stillage per tonne of corn meal for mashing.
- In a typical fermentation process, approximately 360 mg of nitrogen per L of mash is required for the yeast to grow (Jacques, Lyons, & Kelsall, 2003). Missing nitrogen is typically fed to the process as urea.
- The mash is fed to a cooking stage. Here, the mash is typically heated to approximately 104-107° C. (Walker, Abbas, Ingledew, & Pilgrim, 2017), then the temperature is reduced to approximately 85° C. in a flash chamber and the starch is digested with the addition of enzymes. In this regard, a mash temperature of far above the gelatinization temperature of corn is set; this is 62-72° C. for standard corn or 67-80° C. for corn with a high amylose content (Walker, Abbas, Ingledew, & Pilgrim, 2017).
- The mash from the cooking stage is fed to a fermentation step and the digested starch is converted by the yeasts into ethanol at between 25-35° C. (Walker, Abbas, Ingledew, & Pilgrim, 2017). The mass fraction of unconverted starch, the residual starch content, is less than 1.5%.
- Approximately 4% of the sugar and starch in the corn meal (Medina et al., 2009) is transformed into the unwanted by-product glycerin instead of ethanol; this corresponds to approximately 24 kg of glycerin per tonne of corn meal.
- The ethanol-containing mash from the fermentation step is fed to a distillation step at approximately 108° C. (Walker, Abbas, Ingledew, & Pilgrim, 2017) and the ethanol is removed from the mash. The ethanol-depleted mash formed thereby is known as whole stillage.
- The entirety of the whole stillage is fed to a solid-liquid separation step, usually decanter centrifuges. The TS content of the solid phase, hereinafter termed wet cake, is approximately 29-39% (Walker, Abbas, Ingledew, & Pilgrim, 2017) and the TS content of the liquid phase, hereinafter termed the thin stillage, is approximately 4.4-7.8% (Jacques, Lyons, & Kelsall, 2003).
- A portion of the thin stillage is used for mashing the corn meal. The remainder is evaporated to form what is known as syrup and the condensate is used as a process liquid for mashing. Corn oil can be separated from the syrup and can be recovered separately.
- Syrup and wet cake are used as animal feed. Syrup and wet cake are often dried, but can also be used moist as animal feed. In total, approximately 0.25 t dry matter of animal feed per tonne of corn meal is typically produced.

This standard process suffers from the following disadvantages:

- The cooking stage and distillation step are carried out at high temperatures, which leads to a high heat energy consumption.
- Solid-liquid separation of the entire amount of generated whole stillage leads to a high electrical energy consumption.
- The thin stillage is evaporated, in order to obtain process liquids, which leads to a high heat energy consumption.
- Typical further drying processes for the syrup and wet cake bring about a high heat energy consumption, but are necessary in typical configurations for the units in order to obtain a more attractive animal feed.
- Nitrogen has to be added in the form of urea or similar chemicals.
- The energy and chemical consumptions mentioned have a negative effect on the greenhouse gas balance for the fuels which are produced. An example of the quantification of the negative effects is the carbon intensity score (CI score) from the California Low-Carbon Fuel Standard. The CI score is a measure of the greenhouse gas emissions of fuels in grams of carbon dioxide equivalents ($gCO_2e$). A typical ethanol unit in the USA produces fuels with a CI score of approximately 79 gCO2e/MJ (https://ww3.arb.approximatelygov/fuels/lcfs/lcfs_meetings/01312017discussionpa per_e-toh.pdf (Appendix A, accessed on 17.06.2020). The production process in the ethanol unit makes approximately 32 $gCO_2e/MJ^1$ of this, the remainder is from other emissions in the process line such as, for example, corn cultivation.
- A typical ethanol unit has a high water consumption of approximately 2.7 L of fresh water per L of ethanol (Mueller, 2010), which corresponds to approximately 1.2 $m^3$ per tonne of corn meal.

Cooking stages at temperatures below the gelatinization temperature of starches, what are known as cold mash processes, are known and bring about a lower heat energy consumption, but lead to losses which are too high because of residual starches and the risk of bacterial contamination. Comminution of the particle size of the corn meal, changing the pH and greater use of enzymes can reduce these losses and disadvantages (Walker, Abbas, Ingledew, & Pilgrim, 2017). These known measures alone, however, have not been enough in the past, and so the cold mash process has been replaced by the hot mash process.

Furthermore, processes are known which reduce the energy consumption for animal feed production by processing stillage into biogas instead of into animal feed. EP 2 501 818 B1 describes a process in which the stillage from an ethanol unit is fed to a biogas unit and a portion of the outflow from the biogas unit is recycled directly to the ethanol unit. U.S. Pat. No. 8,962,309 B2 describes a biogas unit with different types of biogas fermenters for thin stillage and wet cake. The biogas fermenters therein should be operated at an ammonium concentration of less than 6000 ppm NH4-N. WO 2013/000925 A1 describes a process in which thin stillage is fed to a biogas fermenter of the continuous stirred tank reactor (CSTR) type with a mean hydraulic residence time of 1-20 days.

The problem to be solved by the invention defined in claim 1 is to operate a combination of a bioethanol unit and a biogas unit which saves energy, water and chemicals compared with a typical ethanol unit as described above and which, despite the energy savings, has high ethanol yields per tonne of corn meal. In addition, the use of outflow from the biogas unit as process liquids for the ethanol unit should not have a negative effect on the ethanol fermentation.

SUMMARY OF THE INVENTION

The present invention engages with the problem set out above and solves it by providing a method for carrying out the combined operation of a bioethanol production unit and a biogas unit with the steps defined in claim 1:
 a) mashing corn meal from a dry milling step with at least 0.1 t of dry matter in the form of whole stillage and at least 0.1 $m^3$ of outflow from the biogas unit per tonne of corn meal,
 b) feeding the mash from a) to a cooking stage with mash temperatures below the gelatinization temperature of the starch in the corn meal, followed by an ethanol-forming fermentation step and then feeding the fermented mash to a distillation step,
 c) feeding the whole stillage from b) to the mashing step in a) and to the biogas unit.

In step a), corn meal from a corn dry milling step is mashed with liquids. These liquids consist of at least 0.1 t TS of whole stillage and at least 0.1 $m^3$ of outflow from the biogas unit per tonne of corn meal.

Surprisingly, it has been shown that because of the high recycle of dry matter in the form of whole stillage, the advantages of energy savings for the cooking stage and the mash distillation step at low temperatures can be obtained and at the same time, low residual starch contents in the fermented mash, and thus lower ethanol yield losses, are possible. Furthermore, because of the high recycle, the mass fraction of starch and sugar, which is converted into the unwanted by-product glycerin, is reduced from a typical 4% to less than 2.5%. In addition, because of the high recycle of whole stillage, the availability of nitrogen for yeast growth is increased. In this manner, high ethanol yields of more than 435 liters per tonne of corn meal can be obtained.

The recycle of outflow from the biogas unit has the advantage that savings can be made as regards fresh water as well as process liquids. In a typical ethanol unit, process liquids are obtained in an energy-intensive manner by the evaporation of thin stillage.

In step b), the mash from step a) is fed to a cooking stage in which the mash is heated to temperatures below the gelatinization temperature of the starch in the corn meal. This results in significant savings in energy compared with typical cooking stages at 104-107° C. The mash from the cooking stage is fed to a fermentation step in which ethanol is formed. The ethanol-containing mash from the fermentation step is then fed to a distillation step in which the ethanol is separated out.

In step c), a portion of the ethanol-depleted mash from the distillation step, what is known as the whole stillage, is fed without the typical solid-liquid separation directly to the mashing step a) and to the biogas unit. Compared with typical solid-liquid separation of the whole stillage in its entirety, this means that savings are made as regards the electrical energy for the solid-liquid separation of whole stillage and a large proportion of the residual starch from the fermentation step is recycled which would otherwise no longer be available for ethanol formation because it would have been used as animal feed.

DETAILED DESCRIPTION OF THE INVENTION

Definitions

In the context of the present invention, the term "dry matter" (TS) should be understood to mean the solid residue which is obtained after removing the solvent (for example water or ethanol) from a suspension (for example from stillage) or from a solution. This means that the solid residue should be understood to mean all of the previously dissolved or suspended solids (for example raw proteins, yeast and salts). The mass of the dry matter is known as the dry mass and can be given in kilograms. The term "dry matter content" (TS content) should be understood to mean the percentage mass fraction of the dry matter with respect to the total mass of the suspension (for example the stillage) or solution.

In the context of the present invention, the term "stillage" should be understood to mean the residue from distillation of an ethanol-containing grain mash. The term "whole stillage" is synonymous with "stillage".

In the context of the present invention, the term "solid-liquid separation" should be understood to mean a process which separates a suspension (for example stillage) into a two-phase system comprising a solid phase and a liquid phase. The solid-liquid separation step may advantageously be carried out in a separator or decanter. The term "solid phase" should be understood, in a two-phase system, to mean the phase which has the higher dry matter content. A solid phase in this regard may include a suspension or a sedimented solid (residue). The term "liquid phase" in a two-phase system should be understood to mean the phase which has the lower dry matter content. In this regard, a liquid phase may include a suspension or a clear solution.

In the context of the present invention, the term "thin stillage" should be understood to mean a liquid phase produced by solid-liquid separation of whole stillage. The TS content of a thin stillage can advantageously be at least 8%. The term "wet cake" as used in the context of this invention is defined as the solid phase which is separated from the stillage by solid-liquid separation.

In the context of the present invention, the term "outflow solid" should be understood to mean the solid phase which is separated from the outflow from a biogas fermenter by solid-liquid separation.

In the context of the present invention, the term "ammonium nitrogen content" (NH4-N content) should be understood to mean the mass fraction of nitrogen in the form of ammonium in a sample. In order to measure the NH4-N content of a sample, the sample is made basic with sodium hydroxide and then distilled with steam. Ammonia is driven out of the sample and trapped in a boric acid receiving tank. The mass fraction of ammonium nitrogen is determined by titration of the borate, which is formed, using dilute hydrochloric acid.

DESCRIPTION OF THE INVENTION

Corn is fed to a dry milling step in order to reduce the particle size. In a preferred embodiment, the method in accordance with the invention may be configured in a manner such that the mass fraction of particles with a particle size of <0.5 mm following milling is at least 60%, preferably at least 65%, particularly preferably at least 70% of the corn meal. In a further embodiment, the method in accordance with the invention may be configured in a manner such that the mass fraction of particles with a particle size of <0.36 mm after milling is at least 45%, preferably at least 50%, particularly preferably at least 55%. These significantly smaller particle sizes compared with the prior art have the advantage that the particle surface is more easily accessible to the starch-degrading enzymes. Furthermore, it has surprisingly been shown that in this manner, settling out of particles in the fermenters can be significantly reduced; this would otherwise lead to residual starch contents in the fermented mash which were too high and to losses of productivity when using a cold mash process.

The corn meal from the dry milling step is mashed with different fluids. These fluids are at least whole stillage and outflow from the biogas unit. In addition, other fluids may be involved, for example thin stillage or process liquids.

Surprisingly, it has been shown that because the recycle of dry matter in the form of whole stillage into the mashing step is high, the advantages of the energy savings of the cooking stage and mash distillation at low temperatures can be obtained and at the same time, low ethanol yield losses due to residual starch are possible. In a preferred embodiment, the method is configured in a manner such that per tonne of corn meal in the distillation step, at least 400 liters of ethanol, preferably at least 425 liters of ethanol, particularly preferably at least 435 liters of ethanol are separated. In this regard, at least 0.1 t TS in the form of whole stillage per tonne of corn meal has to be recycled to the mashing step. In a preferred embodiment, the method in accordance with the invention may be configured in a manner such that at least 0.12 t TS, preferably at least 0.14 t TS, particularly preferably at least 0.16 t TS in the form of whole stillage per tonne of corn meal is recycled to the mashing step.

In a further preferred embodiment, the method in accordance with the invention may be configured in a manner such that at least 0.2 t TS, preferably at least 0.3 t TS, particularly preferably at least 0.4 t TS per tonne of corn meal is added in the form of a mixture of thin stillage and whole stillage. In a preferred embodiment, the method in accordance with the invention may be configured in a manner such that the mixture of thin stillage and whole stillage contains a volume fraction of at least 10%, preferably at least 20%, particularly preferably at least 30% whole stillage.

In a preferred embodiment, at least 0.1 t TS, preferably at least 0.2 t TS, preferably at least 0.25 t TS thin stillage pert of mash is recycled. Recycling larger quantities of thin stillage is advantageous compared with using fresh water or process liquids, which are obtained in an energy-intensive manner by the evaporation of thin stillage.

In a preferred embodiment, the method is configured in a manner such that per tonne of corn meal, at least 15 kg, preferably at least 18 kg, particularly preferably at least 20 kg of glycerin is recycled to the mashing step via the whole stillage and thin stillage. Surprisingly, it has been shown that a high recycle of glycerin significantly reduces the fresh formation of glycerin in the ethanol fermentation step. In this manner, less starch or sugar is lost as glycerin and thus the ethanol yield is increased. In a preferred embodiment, the method is configured in a manner such that the recycle of the mixture of thin stillage and whole stillage is selected to be so high that a mass fraction of less than 2.5%, preferably less than 2.3%, particularly preferably less than 2.1% of the starch and sugar present in the corn meal is transformed into glycerin. In a preferred embodiment, the method is configured in a manner such that the recycle of the mixture of thin stillage and whole stillage is selected to be so high that less than 19 kg, preferably less than 17 kg, particularly preferably less than 15 kg of glycerin per tonne of corn meal is produced.

The fraction of outflow from the biogas unit is at least 0.1 $m^3$ per tonne of corn meal. Recycling outflow from the biogas unit has the advantage of economizing on fresh water as well as process liquids. Process liquids are typically obtained hi an energy-intensive manner by the evaporation of thin stillage. Surprisingly, it has been shown that the addition of outflow from the biogas unit to the mashing step does not lead to a severe inhibition of the enzymes and yeasts in the ethanol process if the addition of NH4-N in the form of outflow from the biogas unit is limited. In a preferred embodiment, the method is configured in a manner such that in the mashing step, a maximum of 1000 g, preferably a maximum of 800 g, particularly preferably a maximum of 600 g of NH4-N per tonne of corn meal is recycled via the outflow from the biogas unit. On the other hand, a certain quantity of NH4-IN recycle into the mashing step should be aimed for in order to reduce or dispense with the use of external nitrogen sources such as urea. In a preferred embodiment, the method is configured in a manner such that in the mashing step, at least 100 g, preferably at least 200 g, particularly preferably at least 400 g of ammonium nitrogen per tonne of corn meal is recycled via the outflow from the biogas unit. In a preferred embodiment, the fraction of outflow from the biogas unit per tonne of corn meal is at least 0.2 $m^3$, preferably at least 0.4 $m^3$, particularly preferably at least 0.8 $m^3$.

In a preferred embodiment, the method in accordance with the invention may be configured in a manner such that cellulases and cellulase-forming microorganisms can also be fed from the biogas unit to the mashing step via the outflow from the biogas unit. This has the advantage that in this manner, glucose from the enzymatic hydrolysis of cellulose is made available to the yeasts in the fermentation step, and therefore the ethanol yield can be increased. With the high recycle of whole stillage in accordance with the invention compared with a typical ethanol unit, large quantities of cellulose can also be recycled to the mashing step and thus are available for enzymatic hydrolysis. Preferably, cellulose is present in a mass fraction of at least 5% of the TS of the whole stillage. The recycle of at least 0.1 t TS to the mashing step therefore recycles at least 5 kg of cellulose. The cellulose content in the whole stillage is determined by means of an animal feed analysis in accordance with VDLUFA III. The cellulose content is calculated as the measured ADF value ("acid detergent fiber") minus the measured ADL value ("acid detergent lignin") of a whole stillage sample.

In a further embodiment, the method in accordance with the invention may be configured in a manner such that process liquids in addition to whole stillage and outflow from the biogas unit are used in the mashing step. The process liquids in this regard may be selected from the group comprising: thin stillage, singlings, untreated water, drinking water, water for industrial use, rainwater, ground water, surface water, condensates from the evaporation of thin stillage, process water from $CO_2$ scrubbers, blowdown water from cooling towers, blowdown water and blow-off water from steam production boilers, and mixtures thereof. In a preferred embodiment, the method in accordance with the invention may be configured in a manner such that less than 1.2 m³, preferably less than 0.8 m³, particularly preferably less than 0.2 m³ of fresh water is used per tonne of corn meal.

In a preferred embodiment, the method in accordance with the invention may be configured in a manner such that the pH of the mash is adjusted to less than 4.5, preferably to less than 4.2, particularly preferably to less than 3.8. Surprisingly, it has been shown that despite the cold mash process, contamination by bacteria in the ethanol fermentation can be avoided, proteins are concentrated better, and the availability of cellulose in the corn meal for biological degradation in the ethanol unit and biogas unit can be enhanced.

The mash undergoes a cold mash process, i.e. a cooking stage is carried out in which the mash is heated to temperatures below the gelatinization temperature of the starch in the corn meal. This results in significant energy savings compared with typical cooking stages at 104-107° C. In a preferred embodiment, the method in accordance with the invention may be configured in a manner such that the mash is heated to a maximum of 70° C., preferably to a maximum of 66° C., particularly preferably to a maximum of 64° C.

The mash from the cooking stage undergoes a fermentation step in which ethanol is formed. The ethanol-containing mash from the fermentation is then fed to a distillation step in which ethanol is separated out. This results in significant energy savings compared with typical mash distillation steps at approximately 108° C. In a preferred embodiment, the method in accordance with the invention may be configured in a manner such that the ethanol-containing mash is heated to a maximum of 87° C., preferably to a maximum of 79° C., particularly preferably to a maximum of 68° C. In addition to saving energy, the low temperatures of the cooking stage and distillation step also mean that higher quality proteins are present in the whole stillage. This can be used in order to obtain high value animal feed and foodstuffs from the whole stillage or thin stillage.

The ethanol-depleted mash from the distillation step, what is known as the whole stillage, is re-used in several different ways. A portion is recycled directly to the mashing step. A further portion is fed directly to the biogas unit. The direct use of whole stillage has the following advantages over the typical solid-liquid separation of the entirety of the whole stillage: on the one hand, electrical energy for the solid-liquid separation is saved. On the other hand, a large proportion of the residual starch from the fermentation is recycled; as animal feed or as a substrate for the biogas unit, it would no longer be available for ethanol formation.

In a preferred embodiment, the method in accordance with the invention may be configured in a manner such that a further portion of the whole stillage is fed to a solid-liquid separation step in order to produce thin stillage. In a preferred embodiment, the method in accordance with the invention may be configured in a manner such that a maximum volume fraction of 70%, preferably a maximum of 50%, particularly preferably a maximum of 30% of the whole stillage is fed to a solid-liquid separation step in order to generate thin stillage and wet cake. As an example, the thin stillage may be used in the mashing step, but also for obtaining corn oil, animal feed or foodstuffs. In a further preferred embodiment, the method in accordance with the invention may be configured in a manner such that a further portion of the whole stillage is used as animal feed. The wet cake may also be used as animal feed. In a further preferred embodiment, a maximum of 0.18 t TS, preferably a maximum of 0.12 t TS, particularly preferably a maximum of 0.06 t TS of animal feed per tonne of corn meal selected from the group comprising whole stillage, wet cake, syrup (thin stillage concentrate) and their dried forms are produced. In a preferred embodiment, the method in accordance with the invention may be configured in a manner such that the wet cake is fed to the biogas unit.

In a further preferred embodiment, the method in accordance with the invention may be configured in a manner such that a protein product with a raw protein content (mass fraction of raw protein with respect to TS protein product) of more than 44% is obtained from the thin stillage. In a further preferred embodiment, the method in accordance with the invention may be configured in a manner such that a protein product with a raw protein content (mass fraction of raw protein with respect to TS protein product) of more than 70% is obtained from thin stillage. In a further embodiment, the method in accordance with the invention may be configured in a manner such that corn oil is obtained from thin stillage. In a preferred embodiment, the residual materials from the production of protein products and residual materials from the production of corn oil are fed to the biogas unit.

The biogas unit consists of at least one biogas fermenter of the continuous stirred tank reactor (CTSR) type, in which components of the substrate which is fed in are transformed by a mixed culture of bacteria and archaea to form biogas and by-products such as ammonium. The substrate which is fed in contains at least whole stillage, and in a preferred embodiment may also contain wet cake as well as residual substances from the production of corn oil and from the production of protein products.

Depending on the selected process parameters, specific unwanted metabolites may accumulate during the anaerobic fermentation. These are, inter alia, organic acids such as, for example, acetic acid, propionic acid, butyric acid, isobutyric acid, valeric acid, isovaleric acid and caproic acids, and aromatic components such as, for example, phenol, indole, skatole or cresols. They could have a negative effect on the ethanol fermentation in the ethanol unit and result in odor-related problems.

High ammonium concentrations can inhibit anaerobic fermentation. Typically, then, the NH4-N content is regulated to less than 6000 pm, for example by dilution with process liquids. However, dilution drops the mean residence time of the whole stillage to be fermented in the biogas fermenter, which could result in an unwanted drop in the biogas yield or an accumulation of metabolites. Surprisingly, it has been shown that a stable and efficient anaerobic fermentation of whole stillage is also possible at higher ammonium concentrations. This has the advantage that over-dilution and the associated reduction in the residence time, energy consumption and water consumption are reduced. In a preferred embodiment, the method in accordance with the invention may be configured in a manner such that the ammonium concentration in the biogas fermenters is adjusted to between 6000-9000 ppm, preferably to between 7000-9000 ppm, particularly preferably to between 7500-9000 ppm. In a further preferred embodiment, the method in accordance with the invention may be configured in a manner such that the temperature in the biogas fermenters in the biogas unit is adjusted to below 43° C. This is advantageous, because at higher temperatures, the chemical equilibrium is displaced from ammonium to ammonia and ammonia has a more inhibiting action on anaerobic fermentation.

Surprisingly, it has been shown that even at high ammonium concentrations, a stable fermentation as well as low contents of unwanted metabolites can be obtained by a cascade configuration of biogas fermenters. In a preferred embodiment, the method in accordance with the invention may be configured in a manner such that at least three, preferably at least four biogas fermenters are operated in a cascade in the biogas unit. Infeeding is carried out into the first two stages of the cascade or preferably, into only the first stage of the cascade.

In order to guarantee a stable fermentation as well as low unwanted metabolite contents even at high ammonium concentrations, a sufficiently long mean hydraulic residence time in the biogas unit is vital. In a preferred embodiment, the method in accordance with the invention may be configured in a manner such that the mean hydraulic residence time for the biogas unit is at least 30 days, preferably at least 50 days, particularly preferably at least 70 days. In a preferred embodiment, the method in accordance with the invention may be configured in a manner such that the hydraulic residence time is selected to be as long as required for the concentration of organic acids and aromatic compounds in the outflow from the biogas unit to be a maximum of 450 ppm respectively, preferably a maximum of 300 ppm respectively, particularly preferably a maximum of 150 ppm respectively.

In a further embodiment, the method in accordance with the invention may be configured in a manner such that the outflow from the biogas fermenter undergoes solid-liquid separation and the solid phase, the outflow solids, is discharged. In a preferred embodiment, the outflow solids are used for fertilizer and soil improvement.

In a preferred embodiment, the method in accordance with the invention may be configured in a manner such that the outflow from the biogas fermenter or, preferably, the liquid phase from solid-liquid separation of the outflow from the biogas fermenter, is fed to an ammonia stripping step and the NH4-N content of the liquid phase is reduced to less than 1000 ppm, preferably to less than 750 ppm, particularly preferably to less than 500 ppm. This has the advantage that more outflow from the biogas unit can be recycled to the mashing step without compromising the ethanol fermentation.

In a further embodiment, the method in accordance with the invention may be configured in a manner such that the liquid, ammonium-depleted phase from the ammonia stripping step undergoes an evaporation step. In a preferred embodiment, 0.7 t, preferably 0.8 t, particularly preferably 0.9 t of water per tonne of liquid phase is removed from the liquid, ammonium-depleted phase as an evaporation condensate. This high water extraction is advantageous in that a nutrient-rich concentrate, hereinafter termed the nutrient concentrate, is produced which can be used as a valuable fertilizer. Furthermore, less suspended dry matter is recycled to the ethanol unit via the outflow from the biogas unit, which reduces the viscosity of the mash or gives rise to larger quantities of corn meal or a higher recycle of whole stillage and/or thin stillage. Evaporation of this type is also energetically advantageous compared with typical thin stillage evaporation for the production of process water, because more efficient heat recovery can be carried out.

In a further preferred embodiment, the method in accordance with the invention may be configured in a manner such that lignocellulose-rich biomasses such as, for example, straw, wood, grasses, bagasse or sawdust, can be fed to the biogas unit as a substrate in addition to stillage, the wet cake or the residual substances from the ethanol unit. Compared with mono-fermentation of these substances, this has the advantage that the addition of nutrients such as, for example, sodium or nitrogen which are vital to the growth of microorganisms inn the biogas unit, is reduced, because these are already present inn the residual substances from the ethanol unit.

In a further embodiment, the method in accordance with the invention may be configured in a manner such that a portion of the biogas from the biogas unit is used for the production of process energy for the ethanol unit and/or the biogas unit. As an example, biogas can be converted into electrical process energy in a co-generation unit. As a further example, biogas can be used in a steam boiler for the production of steam. In a preferred embodiment, the method in accordance with the invention may be configured in a manner such that the entire steam requirement for the combined ethanol unit and biogas unit can be provided by biogas produced in the biogas unit. In a preferred embodiment, the method in accordance with the invention may be configured in a manner such that the entire energy requirement for the combined ethanol unit and biogas unit is provided by the biogas produced in the biogas unit, wherein the usual units of the prior art may be used for the production of electrical energy and steam from biogas.

In a preferred embodiment, the combination of a bioethanol unit and a biogas unit may be configured in a manner such that a maximum of 0.5 $m^3$, preferably a maximum of 0.2 $m^3$, particularly preferably a maximum of 0.1 $m^3$ of effluent is produced per tonne of corn meal, which effluent is discharged from the combined bioethanol unit and biogas unit.

In a preferred embodiment, the method in accordance with the invention is configured in a manner such that the biogas is fed to a biogas purification step in which at least $CO_2$ and biomethane are obtained as products. As an example, the biomethane may be compressed and fed into a natural gas grid or used as a vehicle fuel.

BRIEF DESCRIPTION OF THE FIGURES

The invention will now be described in more detail with the aid of two exemplary embodiments and associated drawings, in which.

Exemplary Embodiment 1

Figure 1:
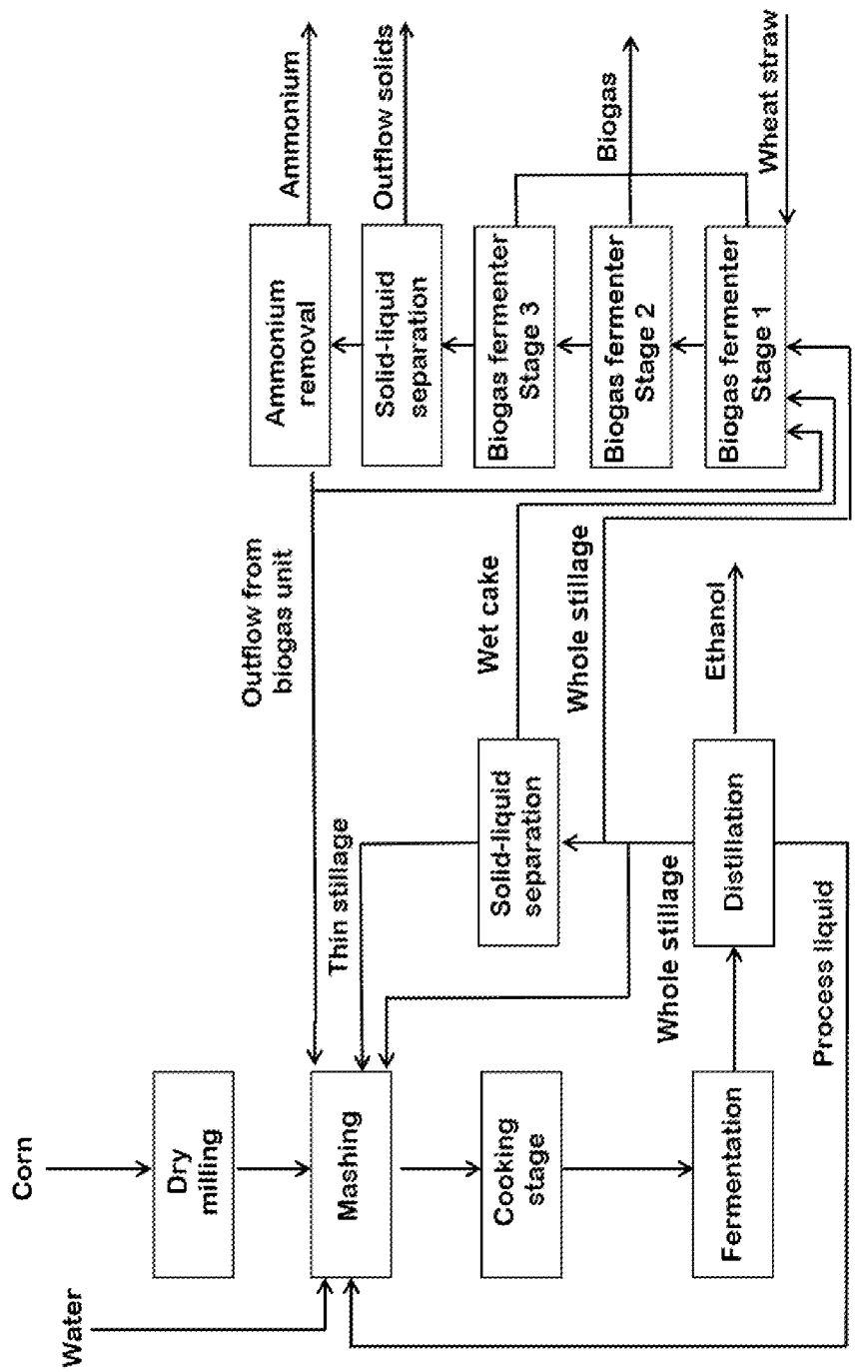
FIG. 1 and FIG. 2 diagrammatically describe the process workflow for embodiments in accordance with the invention.

FIG. 1 shows a diagrammatic representation of the method without the production of animal feed, foodstuffs and corn oil. Table 1 shows the composition of the corn meal for this exemplary embodiment. Table 2 shows the mass flow rates for this exemplary embodiment.

Step 1: Corn is fed to a dry milling step. The corn has a mass fraction of 60% of particles of less than 0.5 mm and a TS content of 85%.

TABLE 1

Corn meal composition

| | Mass fraction of original substance (OS) | Mass fraction of TS |
|---|---|---|
| Water | 15.00% | |
| Starch | 60.90% | 71.65% |
| Sugar | 2.20% | 2.59% |
| Protein | 8.10% | 9.53% |
| Fat | 3.70% | 4.35% |
| Lignocellulose | 8.90% | 10.47% |
| Ash | 1.20% | 1.41% |
| Total | 100.0% | 100.0% |

Step 2: 1.0 t/h of corn meal is mashed with 0.4 t/h of outflow from the biogas unit, 0.8 t/h of whole stillage, 1.6 t/h of thin stillage and 0.46 t/h of process liquid from the ethanol unit and 0.12 t/h of water (for example drinking water). The outflow from the biogas unit, whole stillage, thin stillage and process liquids, has TS contents of 4%, 20.5%, 15% and approximately 0%. Thus, per tonne of corn meal, approximately 0.4 m$^3$ of outflow from the biogas unit, 0.16 t TS of whole stillage, and 0.4 t TS of mixed stillage (whole stillage and thin stillage) is fed to the mashing step. The outflow from the biogas unit has a NH4-N concentration of 500 ppm. In this regard, 200 g of NH4-N in the form of outflow from the biogas unit per tonne of corn meal is fed to the mashing step. The pH is adjusted to 4.2 using sulfuric acid and enzymes for digesting the starches are added (not shown in FIG. 1 and the mass balance of Table 2).

Step 3a: The mash from step 2 is fed to a cooking stage and heated to 60° C.

Step 3b: The mash from step 3a is cooled to below 30° C. Glucoamylase and yeast are added (not shown in FIG. 1 and mass balance of Table 2) and starch is converted into ethanol in the fermentation step.

Step 3c: The ethanol-containing mash is fed to a distillation step at 67° C. and 0.344 t/h of ethanol is removed from the mash (corresponds to 436 liters per tonne of corn meal). The stream of ethanol is freed from water in further steps and the stream of water is fed to the mashing step as the process liquid. The ethanol-depleted mash, the whole stillage, from the distillation step is fed to the mashing step at 0.8 t/h (step 2), to the biogas unit at 0.14 t/h (step 5) and to the solid-liquid separation step at 2.3 t/h (step 4).

Step 4: 2.3 t/h of whole stillage from step 3 undergoes a solid-liquid separation step in a decanter centrifuge. This produces thin stillage and wet cake. The thin stillage is recycled to the mashing step (step 2); the wet cake is fed to the biogas unit (step 5).

Step 5a: Whole stillage from step 3 and wet cake from step 4 and 0.14 t TS/h of wheat straw are fed to the biogas fermenter of the first stage. The outflow from the biogas fermenter of the first stage is fed to the biogas fermenter of the second stage. The outflow from the biogas fermenter of the second stage is fed to the biogas fermenter of the third stage. Biogas is produced in all three stages. 1.3 MW of biogas is formed in the entire biogas unit. The mean hydraulic residence time for the biogas unit as a whole is 70 days.

Step 5b: The outflow from the biogas fermenter of the third stage of step 5a is fed to a decanter centrifuge of a solid-liquid separation step. Outflow solids are thus formed which are discharged from the biogas unit.

Step 5c: The liquid phase from step 5b is fed to an ammonia stripping step (ammonium removal). Here, ammonia is removed from the liquid phase and the NH4-N content falls to 500 ppm. The ammonium which is removed is discharged from the biogas unit in the form of ammonium sulfate. 0.4 t/h of outflow with a 500 ppm NH4-N content was fed to the mashing step (step 2). A portion of the outflow was recycled to the biogas fermenter in step 5a, in order to adjust the NH4-N concentration in the biogas fermenter to 6000-9000 ppm. The concentrations of organic acids and aromatic compounds in the outflow from the biogas unit is a maximum of 150 ppm respectively.

Energy balance: The biogas which is obtained from the biogas unit covers the entire energy requirement for the combined bioethanol and biogas unit. For the fuels produced, this means that the CI score is significantly improved compared with a typical bioethanol unit. In a typical bioethanol unit, the energy consumptions increase the CI score by approximately 20-25 gCO$_2$e/MJ.

Water consumption: The freshwater requirement for the unit is only approximately 0.1 m$^3$ per tonne of corn meal, which corresponds to a reduction in fresh water by one order of magnitude compared with a typical bioethanol unit.

TABLE 2

Mass flow rates for Exemplary embodiment 1

| | t/h | t TS/h | Parameters |
|---|---|---|---|
| Dry milling (step 1) | | | |
| Corn maize, in | ~1 | ~0.85 | |
| Corn meal to step 1 | 1.00 | 0.85 | |
| Mashing (step 2) | | | |
| Corn meal from step 1 | 1.00 | 0.85 | |
| Biogas unit outflow from step 5 | 0.40 | 0.02 | ~0.4 m$^3$ per t corn meal |
| Whole stillage from step 3 | 0.80 | 0.16 | 0.16 t TS whole stillage per t corn meal |
| Thin stillage from step 4 | 1.60 | 0.24 | |
| Mixed stillage (whole stillage and thin stillage, calculated) | 2.40 | 0.40 | 0.40 t TS mixed stillage (whole stillage and thin stillage) per t corn meal |
| Process liquid | 0.46 | ~0 | |
| Water | 0.12 | ~0 | |

Exemplary Embodiment 2

Figure 2:
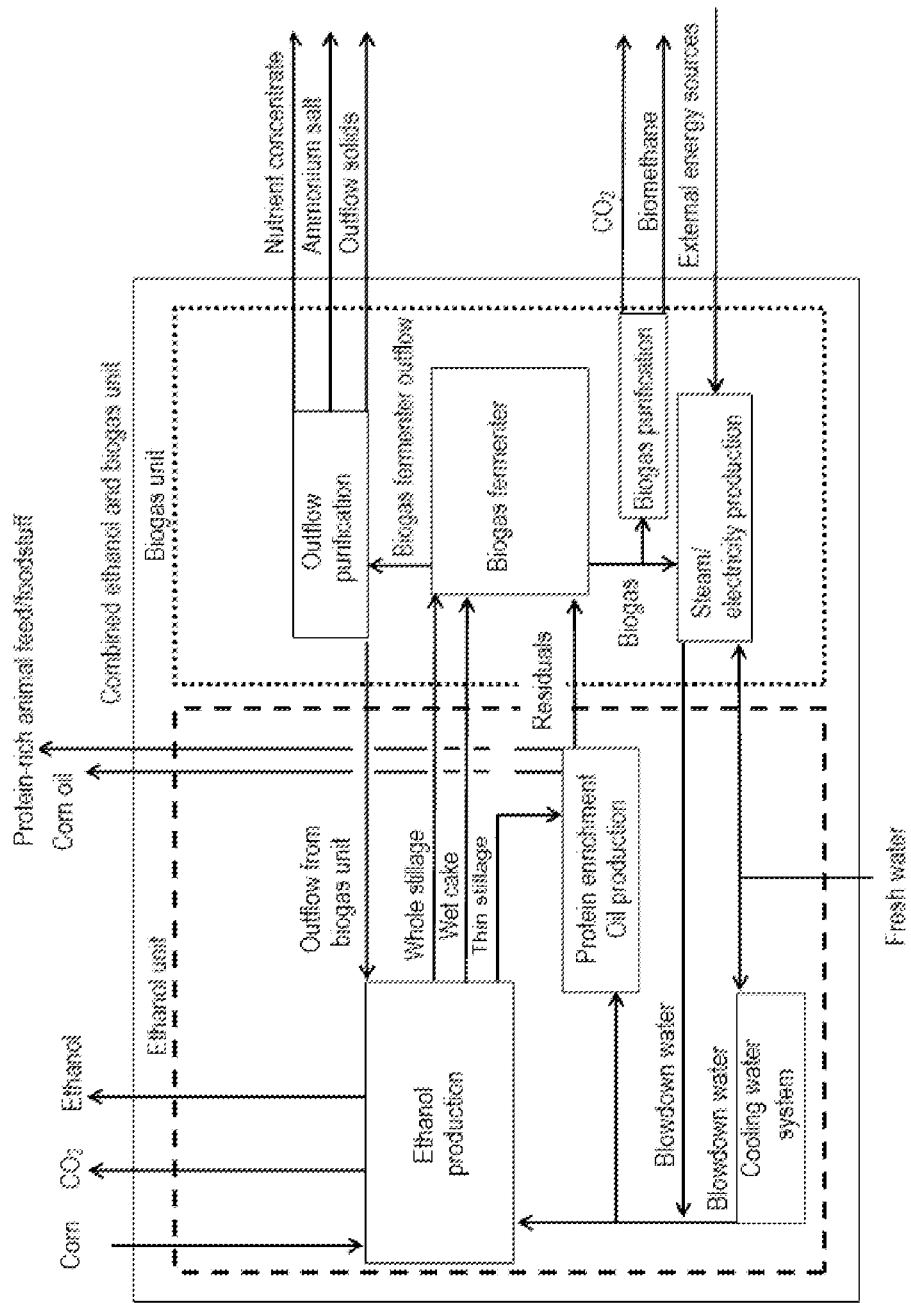

FIG. 2 shows a diagrammatic representation of the method with the production of high added value, protein-rich animal feed and foodstuffs and corn oil.

Step 1a: Corn is fed to the ethanol production step. This contains the process steps of dry milling, mashing, fermentation, distillation and solid-liquid separation of a portion of the whole stillage. Process water is fed in the form of blowdown water from the cooling water system and blowdown water from the steam production system, as well as outflow from the biogas unit. The products are ethanol and carbon dioxide, and whole stillage, wet cake and thin stillage as intermediate products.

Step 1b: High added value, protein-rich animal feed and foodstuffs as well as corn oil are obtained as products from the thin stillage from step 1a. In this regard, "protein-rich" means that the raw protein content (mass fraction of protein in TS) with respect to the thin stillage has been increased using suitable processes. Residual substances are obtained as intermediate products and have a lower raw protein content than the thin stillage.

Step 2a: Whole stillage and wet cake from step 1a as well as residual substances from step 1 b are fed to the biogas fermenters. Biogas fermenter outflow as well as biogas are obtained as intermediate products.

Step 2b: The biogas from step 2a is used for the production of process energy (steam, electricity) and/or are fed to a biogas purification step in which biomethane and carbon dioxide are obtained as products.

Step 2c: The biogas fermenter outflow from step 2a is fed to an outflow purification step. In a solid-liquid separation step, an outflow solid is produced as a product which, for example, could be used as a high added value fertilizer and soil improver. The liquid phase is fed to an ammonia stripping step in which an ammonium salt, optionally as an ammonium salt solution, is obtained as a product. The ammonium-depleted, liquid phase is fed to an evaporation step in which a nutrient concentrate is obtained as a product which, for example, could be used as a fertilizer. An outflow with a reduced nutrient, ammonium and solids fraction compared with the biogas fermenter outflow is obtained from the condensates from the evaporation step as an intermediate product.

Energy balance: Depending on the quantity of corn oil and animal feed/foodstuffs produced, the biogas produced in the biogas unit may be sufficient to cover the entire energy requirement for the combined ethanol unit and biogas unit. External energy sources might be necessary.

Water consumption: The freshwater requirement for the unit is only approximately 0.1 m$^3$ per tonne of corn meal, which corresponds to a reduction in fresh water of about one order of magnitude compared with a typical bioethanol unit.

BIBLIOGRAPHY

Jacques, K., Lyons, T., & Kelsall, D. (2003). The Alcohol Textbook 4$^{th}$ Edition. Nottingham, United Kingdom: Nottingham University Press.

Victor Guadalupe Medina, Marinka J. H. Almering, Antonius J. A. van Maris, Jack T. Pronk. Applied and Environmental Microbiology December 2009, 76 (1) 190-195; DOI: 10.1128/AEM.01772-09.

Mueller, S., 2010b, Detailed Report: 2008 National Dry Mill Corn Ethanol Survey, Energy Resource Center, University of IL at Chicago, May.

Walker, G., Abbas, C., Ingledew, W., & Pilgrim, C. (2017). The Alcohol Textbook 6$^{th}$ Edition. Duluth, Ga., USA: Lallemand Biofuels & Distilled Spirits.

The invention claimed is:

1. A method for carrying out the combined operation of a bioethanol production unit and a biogas unit, wherein:
   a) corn meal from a dry milling step is mashed with at least 0.1 t of dry matter in the form of whole stillage and at least 0.1 m$^3$ of outflow from the biogas unit per tonne of corn meal, whereby at least 100 g of ammonium nitrogen per tonne of corn meal is recycled via the outflow from the biogas unit,
   b) the mash from 1a) is fed to a cooking stage with mash temperatures below the gelatinization temperature of the starch in the corn meal, followed by an ethanol-forming fermentation step and then feeding the fermented mash to a distillation step,
   the whole stillage from 1b) is fed to the mashing step in a) and to the biogas unit.

2. The method as claimed in claim 1, wherein at least 0.2 t of dry matter in the form of whole stillage per tonne of corn meal is added to the mashing step in I1a) in the form of a mixture of thin stillage and whole stillage.

3. The method as claimed in claim 1, wherein at least 0.12 t of dry matter in the form of whole stillage per tonne of corn meal is recycled to the mashing step in 1a) in the form of whole stillage.

4. The method as claimed in claim 1, wherein at least 0.1 t of dry matter in the form of thin stillage per t of mash is recycled to the mashing step in 1a).

5. The method as claimed in claim 1, wherein the cooking stage in 1b), the mash is heated to a maximum of 70° C.

6. The method as claimed in claim 1, wherein the corn meal in 1a) from a dry milling step has a mass fraction of at least 60% of particles with a particle size of <0.5 mm.

7. The method as claimed in claim 1, wherein the pH of the mash in 1a) is adjusted to less than 4.5.

8. The method as claimed in claim 1, wherein the ammonium nitrogen content in the biogas fermenters of the biogas unit is kept at between 6000-9000 ppm.

9. The method as claimed in claim 1, wherein the mean hydraulic residence time for the biogas unit is at least 30 days.

10. The method as claimed in claim 1, wherein the proportion of outflow from the biogas unit per tonne of corn meal in 1a) is at least 0.2 m$^3$.

11. The method as claimed in claim 1, wherein the distillation step in 1b), at least 400 liters of ethanol are separated per tonne of corn meal.

12. The method as claimed in claim 1, wherein the mashing step in 1a), a maximum of 1000 g of ammonium nitrogen per tonne of corn is recycled via the outflow from the biogas unit.

13. The method as claimed in claim 1, wherein less than 1.2 m$^3$ of fresh water is used per tonne of corn meal.

14. The method as claimed in claim 1, wherein at least 15 kg of glycerin per tonne of corn meal is recycled to the mashing step via the whole stillage and thin stillage.

15. A method for carrying out the combined operation of a bioethanol production unit and a biogas unit, wherein:
   a) corn meal from a dry milling step is mashed with at least 5 kg of cellulose in the form of whole stillage and at least 0.1 m$^3$ of outflow per tonne of corn meal from the biogas unit, which latter contains cellulases and/or cellulase-producing microorganisms,
   b) the mash from 16a) is fed to a cooking stage with mash temperatures below the gelatinization temperature of the starch in the corn meal, followed by an ethanol-forming fermentation step and then feeding the fermented mash to a distillation step,
   the whole stillage from 16b) is fed to the mashing step in 16a) and to the biogas unit.

* * * * *